(12) United States Patent
Schilowitz et al.

(10) Patent No.: US 7,172,903 B2
(45) Date of Patent: Feb. 6, 2007

(54) METHOD FOR ON-LINE MONITORING OF LUBRICATING OIL USING LIGHT IN THE VISIBLE AND NEAR IR SPECTRA

(75) Inventors: Alan M. Schilowitz, Highland Park, NJ (US); John S. Szobota, Morristown, NJ (US); Walter D. Vann, Marlton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 663 days.

(21) Appl. No.: 10/379,076

(22) Filed: Mar. 4, 2003

(65) Prior Publication Data

US 2003/0180958 A1 Sep. 25, 2003

Related U.S. Application Data

(60) Provisional application No. 60/363,453, filed on Mar. 12, 2002.

(51) Int. Cl.
*G01N 33/30* (2006.01)
*G01N 33/28* (2006.01)

(52) U.S. Cl. ............ 436/60; 250/343; 356/70; 356/246; 422/81; 422/82.05; 422/82.09; 436/52; 436/61; 436/139; 436/140; 436/141; 436/142; 436/165

(58) Field of Classification Search ........ 250/343, 250/373; 356/70, 246; 422/68.1, 81, 82.05, 422/82.09; 436/43, 52, 60–61, 139–142, 436/165
See application file for complete search history.

(56) References Cited

U.S. PATENT DOCUMENTS 3,584,964 A * 6/1971 Nejame, Jr. ............ 356/244
3,680,962 A * 8/1972 Hayakawa ............ 356/338
3,736,431 A * 5/1973 Childs ............ 250/205
4,319,138 A * 3/1982 Sweet ............ 250/576
4,628,204 A * 12/1986 Maes ............ 250/343
4,649,711 A 3/1987 Sibley et al. ............ 62/129
4,822,166 A * 4/1989 Rossiter ............ 356/246
4,929,847 A * 5/1990 Yamazoe et al. ............ 250/573
4,946,242 A * 8/1990 Tanno et al. ............ 385/88
5,194,910 A 3/1993 Kirkpatrick, Jr. et al. ...... 356/70
5,206,701 A * 4/1993 Taylor et al. ............ 356/325
5,389,524 A * 2/1995 Larsen et al. ............ 435/29
5,691,701 A 11/1997 Wohlstein et al. .......... 340/603
5,739,916 A 4/1998 Englehaupt ............ 356/414
5,828,458 A * 10/1998 Taylor et al. ............ 356/70
5,936,715 A * 8/1999 Shapanus et al. ............ 356/70
6,151,108 A * 11/2000 Kwon et al. ............ 356/70
6,331,704 B1 * 12/2001 Owen ............ 250/339.11
2001/0013247 A1 8/2001 Wilson et al. ............ 73/54.01

FOREIGN PATENT DOCUMENTS

EP 0984278 A1 3/2000
GB 2345067 * 3/2001
JP 2001-221793 * 8/2001

* cited by examiner

*Primary Examiner*—Arlen Soderquist
(74) *Attorney, Agent, or Firm*—Norby L. Foss; Gary P. Katz

(57) ABSTRACT

Oil aging and particulate building in a lubricant other than one exposed to combustion products is monitored by detecting light transmitted through the lubricant at least one, and preferably, two or more preselected wavelengths over a pathlength greater than about 0.5 cm wherein one wavelength is in the near infra-red spectrum and/or one wavelength is in the visible or near infra-red spectrum. The detected light when compared to predetermined values provides an indication of the condition of the lubricant.

8 Claims, 8 Drawing Sheets

METHOD FOR ON-LINE MONITORING OF LUBRICATING OIL USING LIGHT IN THE VISIBLE AND NEAR IR SPECTRA

This application claims the benefit of U.S. Provisional Application(s) No(s).: 60/363,453 filed on Mar. 12, 2002.

FIELD OF INVENTION

The present invention relates to a method for monitoring particulate contamination of a lubricant as well as detecting aging of the lubricant. More particularly the present invention is concerned with an optical method for monitoring on-line the quality of a lubricant other than one in contact with combustion products.

BACKGROUND OF INVENTION

Lubricants, such as industrial oils, are important components of a wide variety of mechanical systems where they provide functions such as lubricating moving parts, transporting force or energy on the mechanical system, protecting parts against wear or even a combination of these.

With use over time these lubricants may become contaminated with substances with which they come into contact, for example by the ingress of foreign substances such as water in the mechanical system, by particulate matter such as that resulting from mechanical wear and the like and oxidative degradation of the base oil and additives used in the lubricants. The net result is a decrease in the performance characteristics of the lubricant with the concomitant negative impact on the mechanical device using the lubricant.

Therefore, in many industrial environments regular lubricant analysis by common laboratory methods is a standard procedure. This necessitates removing a sample of the lubricant and transporting it, typically off-site, for analysis. This procedure normally takes at least three full days before the requisite analysis is completed and a report can be obtained. Such a time lag is highly undesirable.

The art is replete with proposed methods and devices for the on-line evaluation of lubricants, especially engine oils, many of which are based on optical techniques. Because engine oils such as diesel oils are exposed to combustion products such as blow-by gasses and soot they darken severely. For example, many engine lubricants become optically opaque at pathlengths greater than a few millimeters, especially near the end of useful life of the lubricant.

Consequently the optical techniques proposed for on-line evaluation of engine oils employ thin cells typically having a pathlength less than a few millimeters.

Industrial lubricants often are used in larger volumes than engine lubricants and they are not exposed to combustion products. Therefore, darkening from soot is not a significant problem. However, in order to allow a more accurate indication of the condition of an industrial lubricant there is a need to be able to monitor a more representative sample of the lubricant than might be monitored using thin optical cells such as proposed for engine lubricants. Also, there is a need to avoid fluid flow restriction resulting form use of these optical cells.

Thus there remains a need for improvements in determining the condition of industrial lubricants.

An object, therefore, of the present invention is to provide an on-line, real-time, method for monitoring the condition of lubricants that are not exposed to combustion products such as industrial oils.

These and other objects will become apparent from the description which follows.

SUMMARY OF INVENTION

The present invention provides a method for monitoring oil aging and particulate buildup in a lubricant, other than one exposed to combustion products, by detecting light transmitted through the lubricant at a wavelength preselected from a specific range of wavelengths. Another embodiment of the present invention provides a method for monitoring oil aging and particulate buildup in a lubricant, other than one exposed to combustion products, by detecting light transmitted through the lubricant at two or more preselected wavelengths over a pathlength of greater than about 0.5 wherein one wavelength is in the visible spectrum or near infrared spectrum and one wavelength is in the near infra-red spectrum whereby the amount of light detected provides an indication of the condition of the oil.

The present invention provides an improved method of measuring the oxidation and overall degradation of a lubricant using light in the visible or near IR spectra. More specifically, the present invention allows a more representative determination of on-line lubricant conditions to be made by concurrently measuring several oil degradation parameters.

In one embodiment of the current invention, the age, quality and oxidation of a lubricant is determined by measuring light passing through the lubricant in the visible or near IR spectrum (approximately 400 nm to 850 nm). In another embodiment an industrial oil circulating through a mechanical system is passed through an optical cell having a light pathlength greater than 0.5 and the oil in the cell is exposed to light at two wavelengths, one at about 400 run to 850 nm and the other at 875 nm to about 1100 nm and the light passing through the oil is detected and compared to a predetermined value to determine the degradation and particulate condition of the oil.

DETAILED DESCRIPTION OF INVENTION

The present invention is applicable to on-line, real-time, monitoring of the degradation and particulate buildup in industrial oils in use in mechanical systems, i.e., oils other than those exposed to combustion products.

In the past, a common means of determining the extent of oxidation of a lubricant has been to measure the increase in absorbance due to the carbonyl functional group at about 1700–1750 cm−1 which is in the mid infrared portion of the electromagnetic spectrum. However, unexpectedly the inventors found that we could measure oxidation in the visible-near IR region of the spectrum (from 400 nm to 850 nm). This is unexpected because broad spectral features in this part of the spectrum are not due to vibrations or electronic transitions of particular chemical functional groups and therefore do not provide specific chemical functional group information. The advantage of measuring in this region of the spectrum is that a more robust measuring technique with a longer path length can be applied at these wavelengths. For example we can typically use a path length of 1 cm while in the mid IR part of the spectrum a path length of less than 200 microns would be necessary to avoid total absorption of radiation. Larger path lengths are less likely to incur blockage from sludge and particulate. In addition, the mid-IR portion of the spectrum is susceptible to noise from blackbody radiation from very hot oil. This is much less problematic at our preferred wavelengths.

Figure 1:
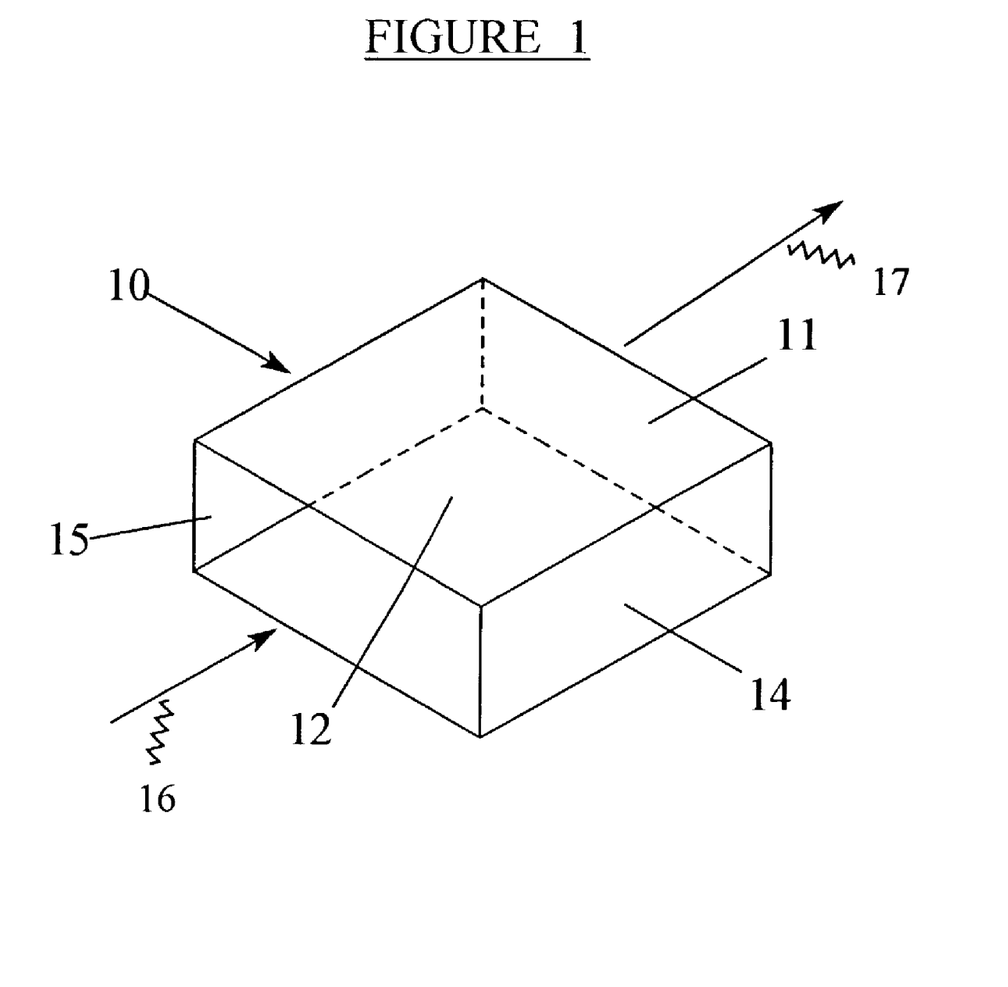
FIG. 1 is a perspective view of an optical cell useful in the present invention.

According to one embodiment of the invention an industrial oil, under conditions of use in a mechanical system, is circulated through an optical cell positioned in any convenient location within the mechanical system. For example, the cell may be a segment of a manifold through which oil is circulated or as part of a by-pass line. A perspective view of our suitable optical cell 10 is shown in FIG. 1. Cell 10 has light transparent top and bottom walls 11 and 12 respectively, made for example of glass or quartz. Cell 10 is provided with side walls 14 and 15. The ends of cell 10 are open to permit the flow of oil through the cell as illustrated by arrows 16 and 17. Means (not shown) are provided to incorporate the cell 10 in fluid communication with oil circulating through a mechanical system (also not shown). The height of side walls 14 and 15 and hence the space between top 11 and bottom 12, is greater than about 0.5 cm and preferably between 0.5 to 1.5 cm.

Figure 2:
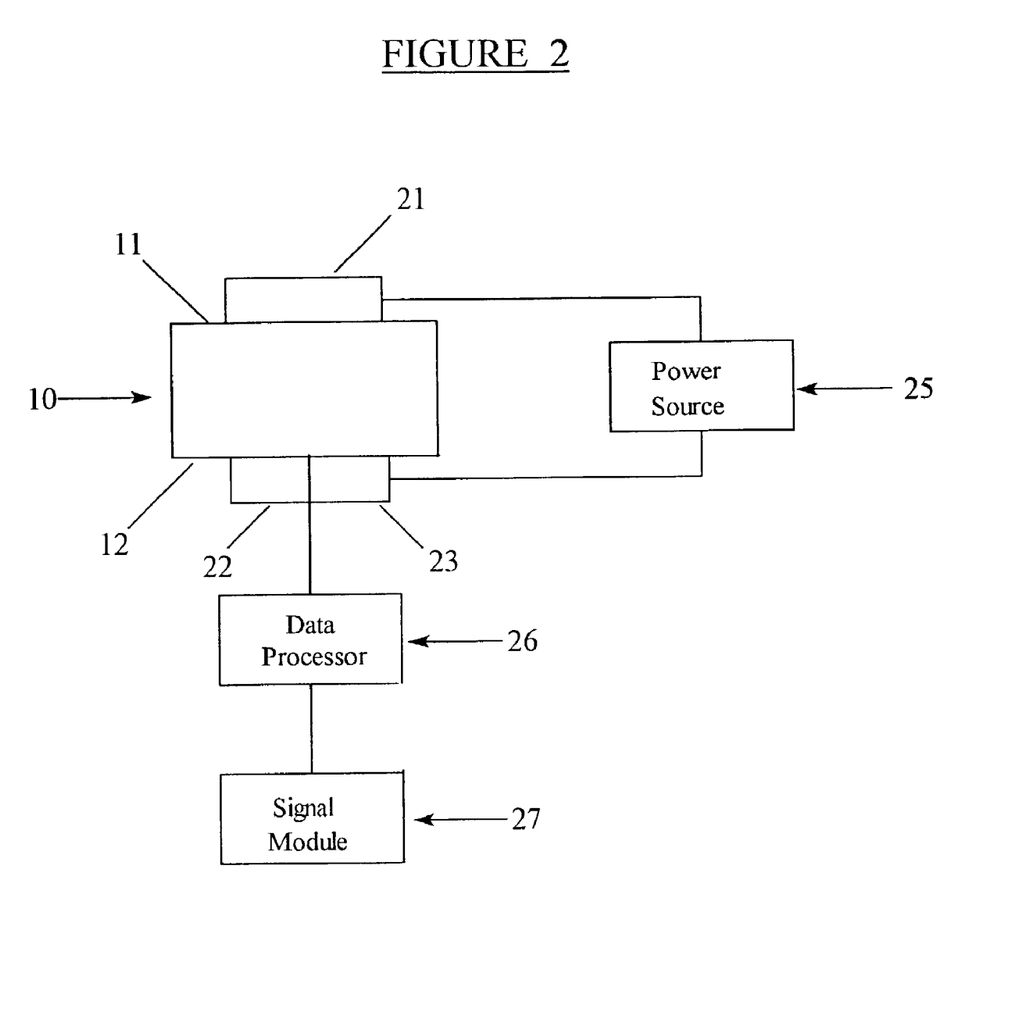
FIG. 2 is a block schematic diagram of an optical system useful in the present invention.

As shown in FIG. 2 positioned on the top 11 of the optical cell 10 is means 21 for emitting light from at least one, and as shown here, two different preselected wavelengths perpendicular to the top 11. Means 21 may be one or two discrete light sources or alternatively a broadband light source provided with filters whereby the light emitted will be at one or two different preselected wavelengths. Positioned on the bottom 12 of cell 10 are at least one, and as shown in this Figure, two light detectors 22 and 23 aligned to detect each respective wavelength of light emitted and passed through the oil and for generating an electrical signal in response to the light detected. In practice, the electrical signal is used to calculate one of transmittance or absorbance. Transmittance, of course, is the percentage of light transmitted by the oil while absorbance is equal to log (transmitted light/incident light). In either case, the light source 21 comprises at least one light emitting diode capable of emitting light at a preselected wavelength and as demonstrated in this example it comprises two light emitting diodes capable of emitting light of preselected wavelengths. As noted before, light source 21 could also be a broadband light source with filters. The detectors are commonly available solid state photodetectors.

Light means 21 and detectors 22 and/or 23 are operably connected to a power source 25 and a data processor 26 for comparing the electrical signal and preferably the transmittance or absorbance to predetermined values for a known degradation and particulate condition of an oil. It is obvious to one skilled in the art that any combination of broadband or discreet light means with any combination of various detectors may be employed.

One embodiment of this invention allows the light to be emitted solely at one wavelength in the visible or near IR range. While the precise wavelength depends upon the lubricant being monitored, the inventors have unexpectedly found that the 400 nm to 850 nm region of the visible-near IR spectrum is useful for determining the oxidation, aging and quality of the oil. In another embodiment of the present invention, light is emitted at two different, preselected wavelengths. One of these is in the visible or near infra-red spectrum, the other in the near infra-red spectrum. The precise wavelengths will depend upon the lubricant being monitored. In general one wavelength will be between about 400 nm and 850 nm and the other between 875 nm and about 1100 nm. The preferred wave lengths for different industrial oils vary, depending on the base stock and additive combinations used. However, a wavelength of about 975 nm is preferred for judging particulate buildup in paper machine oils.

As is shown in FIG. 2, a result display or signal module 27 is operably connected to data processor 26 to provide a visual display of the oil condition or an indication of the remaining useful life. Alternatively a signal such as a bell or alarm may be provided when the oil condition reaches a predetermined state requiring changing of the oil before continuing operating the mechanical system.

Either the signal module 27, the data processor 26 or both may be operably connected to the system by hardwire, wireless transmission means or via the internet.

EXAMPLE 1

Figure 3:
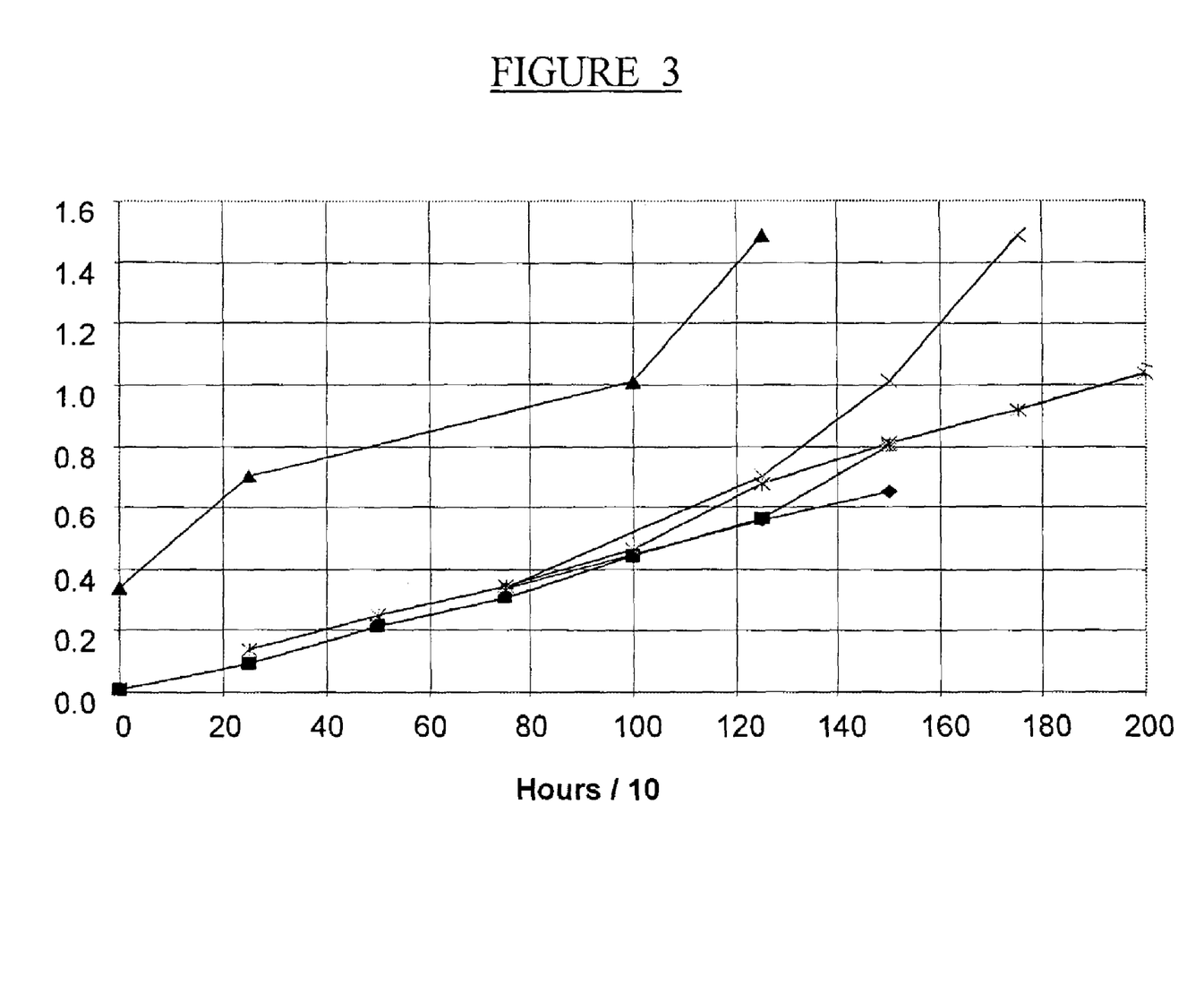
FIG. 3 is a graph of absorbance at 500 nm for several lubricants versus hours on the test rig.

Five different paper machine oils were separately circulated at the same elevated temperature and for substantially the same time period in a test rig designed to simulate oil aging that normally occurs over several years of service in a paper machine. The absorbance of light at 500 nm for each of the oils was periodically measured. A plot of absorbance at 500 nm versus hours on the test rig is shown in FIG. 3. As can be seen, four of the oils start out with an absorbance close to zero while a darker fifth oil starts out with an absorbance of about 0.35. Nevertheless all darken at about the same rate demonstrating that absorbance is an effective measure of oil life.

EXAMPLE 2

Figure 4:
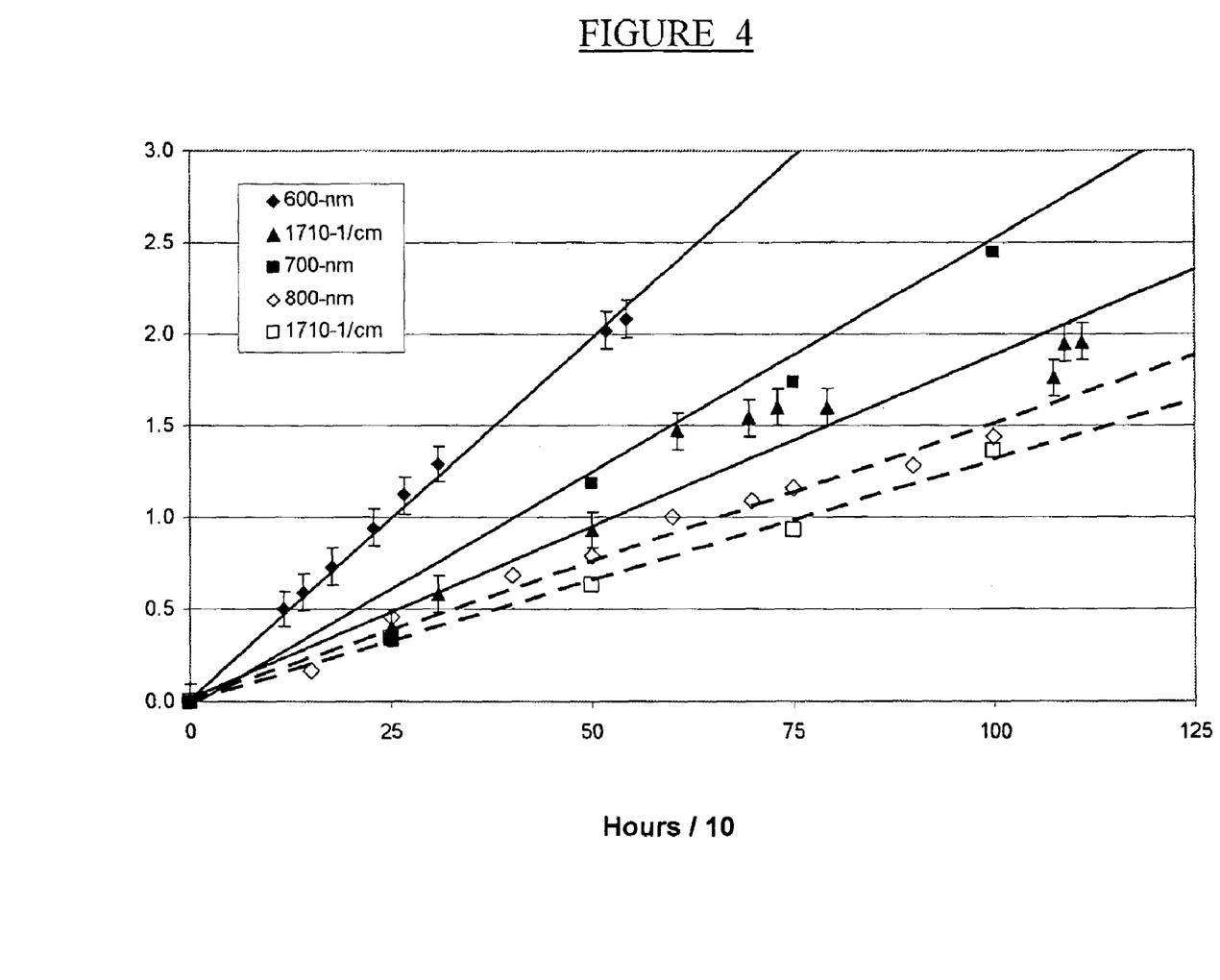
FIG. 4 compares the results from two different progressively aged industrial oils for absorbance vs. time FIG. 5 compares the absorbance vs. time results at various wavelength for a sample.

Two different industrial oils were aged in the laboratory by means of circulating rig tests. The graph in FIG. 4 compares the results from these two progressively aged oils. Off-line infrared measurements for the carbonyl region (1710–1/cm) are compared with on-line measured absorbance of light at 600, 700, and 850 nm. The two sets of data shown in FIG. 4 (represented by solid and dashed lines) were obtained from a turbine oil and a paper machine oil. The different rig tests were designed to age test oils under different conditions.

The graph illustrates that different lubricants and/or conditions have different V-NIR absorbance profiles. In other words, different (or a combination of different) V-NIR wavelengths can be used to track oxidation in different lubricants and under varying conditions.

EXAMPLE 3

Figure 5:
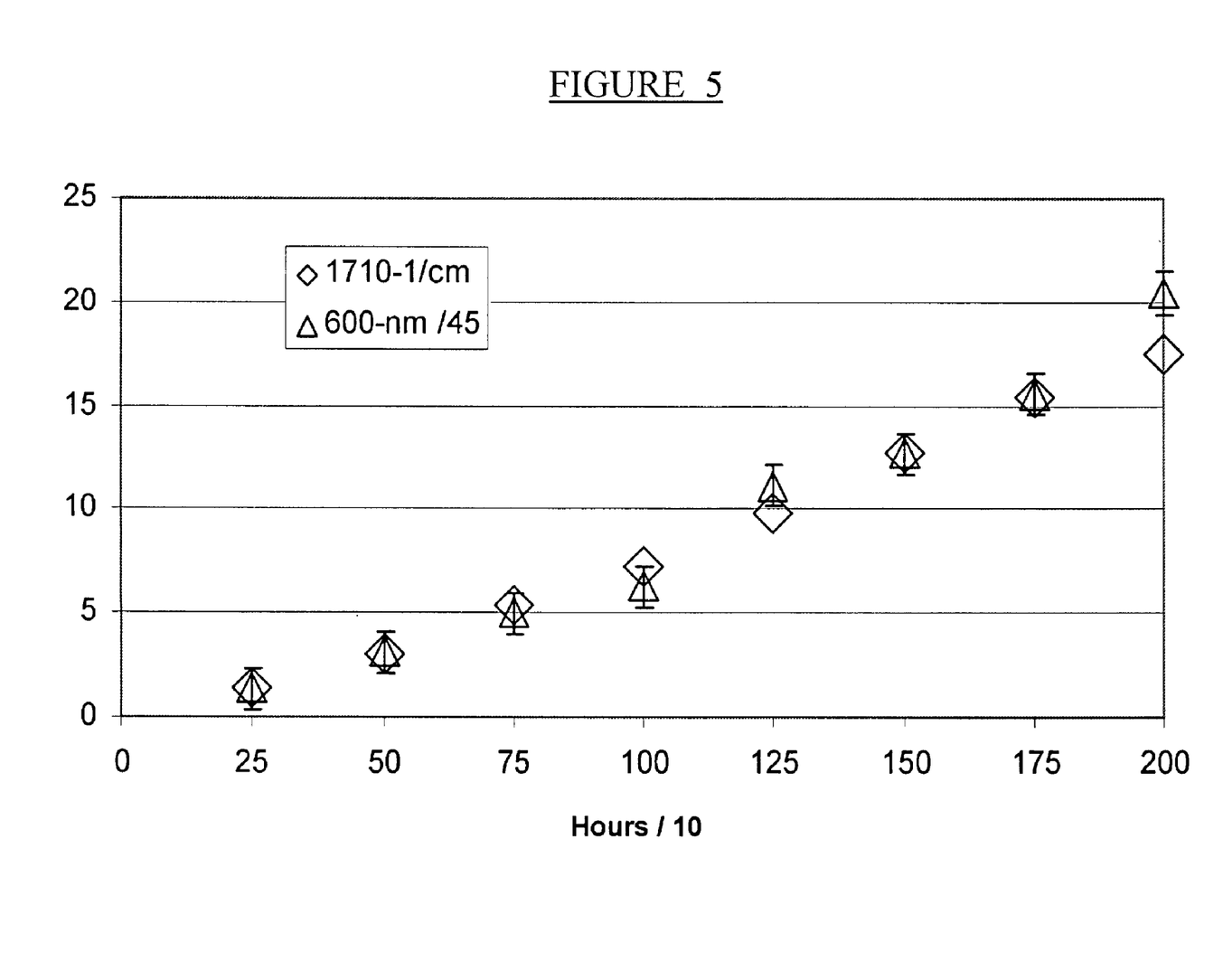

Example 3 shows a third lubricant run under a third set of rig conditions. These data illustrate that this effect is independent of the type of rig test used to age the oil. This example also shows how a simple algorithm (specific to the oil being aged) can provide the correlation between a wavelength in the V-NIR and the degradation of the oil. The results of these tests are shown in FIG. 5. The notation in FIG. 5 (600-nm/45) indicates that the measured value at 600-nm was multiplied by 45 (a simple scaling factor). This number is relative and depends on measurement time, wavelength, and path length.

EXAMPLE 4

Figure 6:
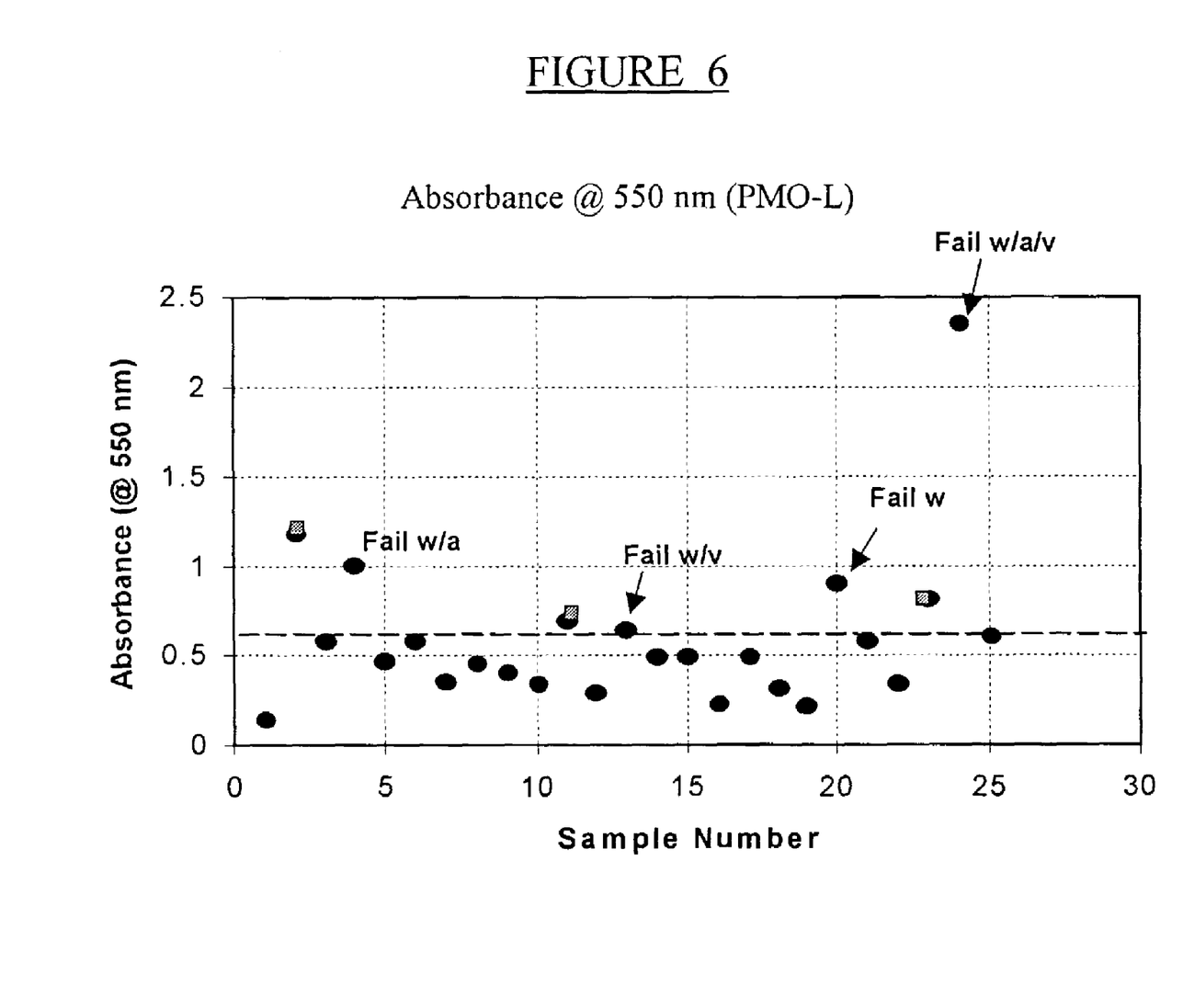
FIG. 6 compares the absorbance at 550 nm for various oils against sample number.

In this example, twenty-five samples of paper machine oils were gathered from operating paper machines. The samples varied in length and type of service. All were analyzed for viscosity, wear metals and additive metals. Four of the oils failed the analysis for one or more of wear, low additive and low viscosity. The absorbance of each of the oils at 550 nm also was determined. All four of the oils that failed the viscosity, wear or additive tests had an absorbance greater than 0.6 while 18 acceptable oils had an absorbance below 0.6. The results of these tests are shown in FIG. 6.

EXAMPLE 5

Figure 7:
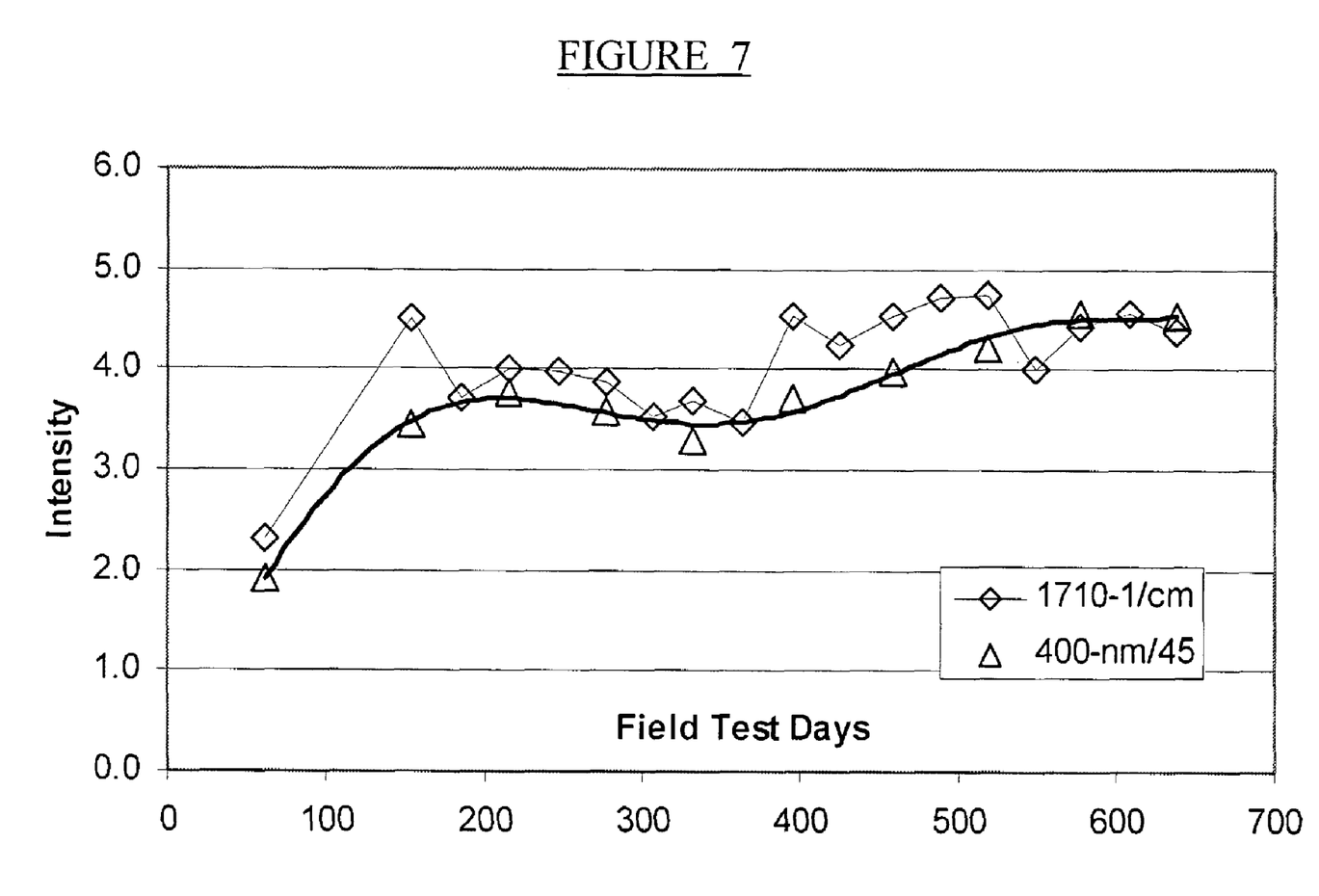
FIG. 7 compares the intensity vs. time at various wavelengths.

FIG. 7 graphically illustrates the con-elation of the infrared absorbance at 1710 $cm^{-1}$ to the Visible-Near Infrared measurements of a fourth lubricating oil from an actual field test. This field test was conducted over a period of almost two years. The oil was very resistant to oxidation after an initial break-in period.

FIG. 7 not only shows how well oxidation is tracked by V-NIR spectroscopy in a real world application, it also illustrates how overall lubricant degradation is more representatively tracked by the V-NIR measurements than a single infrared measurement. The darker smooth curved line in FIG. 7 illustrates the gradual degradation of the oil overtime, compared to the more varied changes observed from the infrared measurements.

EXAMPLE 6

A subset of field samples of paper machine oils of Example 4 were analyzed for particulate level. Particulate levels were measured in three size categories, greater than 2, 5 and 15 microns. When the absorbance of these samples at 550 nm was plotted against the number of particles greater than 2 microns and greater than 5 microns no correlation was found.

Figure 8:
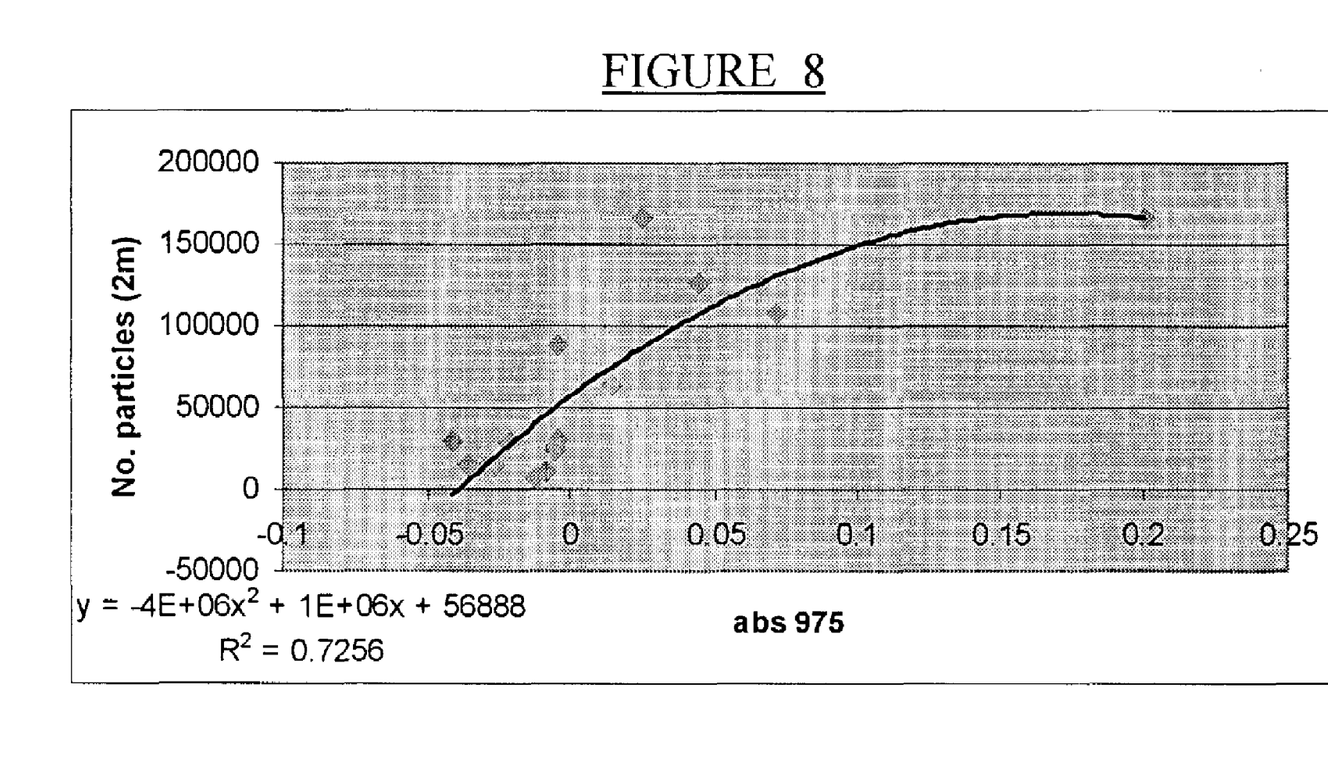
FIG. 8 compares the number of particles in the oil compared to the absorbance at 975 nm.

The absorbance of these samples at 975 nm was also measured and plotted against the number of particles greater than 2 microns. The resulting plot is shown in FIG. 8. This plot shows a high level of correlation especially when a polynomial is used to fit the data points.

What is claimed is:

1. A method for monitoring oil aging and particulate buildup in a lubricant, other than one exposed to combustion products, comprising:
    detecting, on-line and in real-time, light of two or more preselected wavelengths transmitted through the lubricant, at least one wavelength being in the visible or near infra-red spectrum, wherein the wavelength of the visible or near infra-red spectrum is from about 400 nm to about 850 nm, and one other wavelength being in the near infrared spectrum, wherein the wavelength of the near infra-red spectrum is from about 875 nm to about 1100 nm, the light being transmitted over a pathlength of greater than or equal to 0.5 cm; and
    comparing light detected with a predetermined value for each wavelength whereby oil aging and particulate buildup is monitored.

2. The method of claim 1 wherein the pathlength is between 0.5 to 1.5 cm.

3. The method of claim 1 wherein at least one transmittance or absorbance is obtained from the light detected and is compared to a predetermined value.

4. The method of claim 1 wherein the oil is circulated through an optical cell contained in a mechanical system.

5. A method for determining oil aging and particulate buildup in a lubricant, other than one exposed to combustion products, wherein the lubricant is contained in a mechanical system, the method comprising:
    circulating the lubricant through an optical cell positioned within the system, the optical cell having a pathlength of greater than or equal to 0.5 cm;
    exposing the lubricant in the cell to light at two or more preselected wavelengths, one or more wavelengths in the visible or near infra-red spectrum wherein the wavelength of the visible or near infra-red spectrum is from about 400 nm to about 850 nm, and the other in the near infra-red spectrum wherein the wavelength of the near infra-red spectrum is from about 875 nm to about 1100 nm;
    detecting the light passing through the oil for each wavelength with on-line, real-time monitoring;
    comparing the detected light with a predetermined value for each wavelength whereby oil aging and particulate buildup is determined.

6. The method of claim 5 wherein the cell has a pathlength from about 0.5 cm to 1.5 cm.

7. The method of claim 5 wherein at least one of transmittance or absorbance is obtained from the light detected and compared to a predetermined value.

8. The method of claim 5 wherein the circulating, transmitting and measuring are continuous.

* * * * *